United States Patent
Thulin

(10) Patent No.: US 10,130,583 B2
(45) Date of Patent: Nov. 20, 2018

(54) POWDER COMPOSITION FOR TREATING A DISORDER IN THE AUDITORY CANAL OF MAMMALS AND USE THEREOF

(71) Applicant: Pegion Operations Limited, Gzira GZR (MT)

(72) Inventor: Claes Thulin, Stockholm (SE)

(73) Assignee: Pegion Operations Limited, Gzira (MT)

( * ) Notice: Subject to any disclaimer, the term of this patent is extended or adjusted under 35 U.S.C. 154(b) by 0 days.

(21) Appl. No.: 14/784,636

(22) PCT Filed: Apr. 14, 2014

(86) PCT No.: PCT/SE2014/000049
§ 371 (c)(1),
(2) Date: Oct. 15, 2015

(87) PCT Pub. No.: WO2014/171873
PCT Pub. Date: Oct. 23, 2014

(65) Prior Publication Data
US 2016/0081931 A1   Mar. 24, 2016

(30) Foreign Application Priority Data

Apr. 16, 2013  (SE) ...................................... 1350478

(51) Int. Cl.
| | | |
|---|---|---|
| *A61K 9/14* | (2006.01) | |
| *A61K 33/06* | (2006.01) | |
| *A61K 9/00* | (2006.01) | |
| *A61K 31/155* | (2006.01) | |
| *A61K 31/191* | (2006.01) | |
| *A61K 31/7004* | (2006.01) | |
| *A61K 31/7016* | (2006.01) | |
| *A61K 33/08* | (2006.01) | |
| *A61K 31/19* | (2006.01) | |
| *A61K 33/00* | (2006.01) | |

(52) U.S. Cl.
CPC .............. *A61K 9/14* (2013.01); *A61K 9/0046* (2013.01); *A61K 9/143* (2013.01); *A61K 31/155* (2013.01); *A61K 31/19* (2013.01); *A61K 31/191* (2013.01); *A61K 31/7004* (2013.01); *A61K 31/7016* (2013.01); *A61K 33/00* (2013.01); *A61K 33/06* (2013.01); *A61K 33/08* (2013.01)

(58) Field of Classification Search
CPC .............. A61K 2300/00; A61K 31/155; A61K 31/191; A61K 31/7004; A61K 31/7016; A61K 33/06; A61K 33/08; A61K 31/19; A61K 33/00; A61K 9/0046; A61K 9/14; A61K 9/143

See application file for complete search history.

(56) References Cited

U.S. PATENT DOCUMENTS

| | | | |
|---|---|---|---|
| 2005/0009790 A1 | 1/2005 | Sichtnik | |
| 2009/0005339 A1* | 1/2009 | Scholz | ................. A61K 31/045 514/53 |

FOREIGN PATENT DOCUMENTS

| | | |
|---|---|---|
| CN | 101278917 A | 10/2008 |
| GB | 865672 A | 4/1961 |
| JP | S60-163807 | 8/1985 |
| WO | WO 2004/035071 A1 | 4/2004 |

OTHER PUBLICATIONS

Roland et al., "Disorders of the External Auditory Canal", 1997, Journal of the American Academy of Audiology, vol. 8, pp. 367-378.*

L. K. Cole et al., "Evaluation of an Ear Cleanser for the Treatment of Infectious Otitis Extema in Dogs", Veterinary Therapeutics, vol. 4, No. 1, 2003, pp. 12-23.

* cited by examiner

*Primary Examiner* — Michael B. Pallay
(74) *Attorney, Agent, or Firm* — Blank Rome LLP

(57) ABSTRACT

The invention relates to a new powder composition which comprises in admixture: lactic acid, lactose and kaolin, wherein the amount of lactic acid is such that the pH of the powder composition should be within the range of about 3 to 4. Said powder composition may be use as a veterinary drug and in treating and/or preventing a disorder in the auditory canal of dogs and cats.

6 Claims, No Drawings

POWDER COMPOSITION FOR TREATING A DISORDER IN THE AUDITORY CANAL OF MAMMALS AND USE THEREOF

FIELD OF THE INVENTION

The present invention relates to a new powder composition for preparation of a veterinary compound intended for treating and/or preventing a disorder in the auditory canal of mammals, and more particular treating and/or preventing a non-serious disorder in the auditory canal of mammals, particularly dogs and cats, i.e. a disorder not so severe that it requires treatment with antibiotics or other forms of pharmaceuticals, the disorder being selected from the group consisting of otitis externa, pyotraumatic folliculitus and conditions in which the skin is affected in a negative way by an unbalance in the microflora with an abnormal high degree of colonization of fungus and bacteria.

The inventive powder composition is not a powder composition for treatment in the pharmaceutical sense, rather a prophylaxis for ear infections by controlling the microbial overgrowth.

SUMMARY OF THE INVENTION

Otitis externa is known to be one of the most common diseases in the auditory canal/ear canal of mammals, such as dogs and cats, and affects an estimated 15-20 percent of the total canine population. There is greater susceptibility to otitis externa of long-haired, pendulous-eared breeds of dogs rather than of dogs or other animals having erected ears, the latter type of ear being better ventilated.

Clinical signs of otitis externa are foul odor, pruritus, head shaking, lipid/wax depositions and erythema.

Primary causes of otitis externa include, but are not limited to, hypersensitivity, keratinization disorders, foreign bodies, ear gland disorders, and autoimmune disorders. These conditions are responsible for altering the environment of the auditory canal to allow for abnormal colonization of microorganisms. Predisposing factors includes such conditions as pendulous pinnae, stenosis, neoplasms, hair in the ear, excessive cerumen production, trauma, and high humidity.

Other disorders in the auditory canal of mammals are, for instance, pyotraumatic folliculitis and conditions in which the skin is affected in a negative way by an unbalance in the microflora with an abnormal high degree of colonization of fungus and bacteria.

Perpetuating factors include bacteria (primarily *Staphylococcus* spp. and *Pseudomonas* spp.); yeasts (primarily *Malassezia* spp.); and pathologic changes, such as glandular hyperplasia, epithelial folds, neoplasia, edema, mineralization, and fibrosis. These conditions are frequently seen as the cause of ear infections.

Alterations in normal microflora in the ear and skin may play a role as predisposing factors in allowing the overgrowth of *Malassezia*.

*Malassezia pachydermatis* is a common commensal organism of the anal sacs, anus, auditory canal, and skin of dogs. The lipophilic, oval, budding yeast is common etiologic agent in canine otitis externa, and may be found in as many as 36 percent of normal canine auditory canals. Factors favoring its growth include abnormal levels of ceruminous lipids, high humidity, and abnormal cell-mediated immunity. Another prerequisite for optimal growth is a pH in the range of five to eight.

*Staphylococcus Pseudintermedius* is a common commensal organism of oral, nasal, and skin flora in healthy dogs, where it can cause an invasive disease. Its optimal pH level for growth is between 7 and 7.5, and under 4 it will not grow.

The above conditions are normally treated with antibiotics or other types of pharmaceuticals, but in consideration of the widespread, and sometimes excessive, use of antibiotics, bacteria have developed a resistance to antibiotics limiting and even cancelling their antibacterial effect. Therefore, new routes are sought for combating said disorders in the auditory canal, and it would be desirable to find a prophylaxis for otitis externa that both the dog and the owner finds convenient and easy to use.

Furthermore, there are numerous ear cleaners commercially available to veterinaries and pet owners containing a variety of ingredients, such as alcohols, organic acids, propylene glycol, various peroxides, boric acid and detergents in liquid compositions/preparations.

A problem with a liquid composition/preparation is that, when given to the auditory canal of the dog which is relatively long, the dog will shortly afterwards shake its head and much of the liquid composition/preparation is lost. Therefore, extensive massage of the ear/auditory canal must be performed once the liquid composition/preparation is inside the canal. This treatment is however uncomfortable both for the dog and the owner.

Therefore, the present inventor has focused on a powder composition which is less uncomfortable both for the patient/dog and the owner and which has an effect on the growth of microorganisms, particularly fungal growth.

It is known that yeasts will die at a pH of about 3 and *Staphylococcus* spp. at a pH of about 4.

Thus, the present inventor has realized that, by providing a composition which reduces the amount of fat, the degree of moisture and lowering the pH in the auditory canal of the patient, it is possible to reduce or even eliminate the growth of microorganisms therein.

Furthermore, the inventive composition should also be able to be administrated for maintenance treatment so as to avoid ear problems of the above-mentioned types.

More particularly, the inventors are of the opinion that by lowering the pH of the auditory canal to about 4 *Staphylococcus* will die which means that *Malassezia* will no longer have access to nicotinic acid produced by *Staphylococcus*, and by binding moisture *Malassezia* will no longer be able to multiply, and by binding fat, in which the *Malassezia* is "dissolved", will prevent the *Malassezia* from colonizing the cell-wall.

Thus, the concerned microorganisms are sensitive to changes in the physical environment in the ear. Moisture, lipid levels and pH may significantly change the optimal growth conditions and disturb colonization and thus eliminate problems of the auditory canal related to the microorganisms concerned.

The present invention discloses a new powder composition which comprises in admixture: lactic acid, lactose and kaolin, wherein the amount of lactic acid is such that the pH of the powder composition should be within the range of about 3 to 4.

The powder composition according to the invention is for use as a veterinary drug.

The powder composition according to the invention is also for use in treating and/or preventing a disorder in the auditory canal of dogs and cats, the disorder being selected from the group consisting of otitis externa and pyotraumatic folliculitus.

An example of a compound that reduces the pH is lactic acid, and the amount of lactic acid in the composition according to the invention is about 0.01-2, preferably 0.05-1.5, and particularly 0.1-1 percent by weight of the total composition, and having a particle size of about 10-1000 µm, preferably 300-900 µm, and particularly 500-800 µm. Lactic acid is a natural organic acid that has a quick onset as it dissolves rapidly in water.

Examples of compounds that reduce the degree of moisture and may at the same time lower the pH of the auditory canal are mono-, di-, and oligosaccharides. One such example is lactose which binds moisture and is split by the microorganisms into lactic acid, thus creating an acidic environment in the auditory canal, whereby a synergistic effect is obtained together with the lactic acid forming part of the inventive composition. The inventive composition comprises lactose in an amount of about 15-60, preferably 10-55, and particularly 15-50 percent by weight of the total composition, and having a particle size of about 1-200 µm, preferably 7.5-150 µm, and particularly 15-100 µm.

Examples of compounds that bind fat are alkyl polyglucoside, derivative of glucamine and aluminum silicate. Particularly preferred is kaolin, and the inventive composition comprises kaolin in an amount of about 20-80, preferably 30-75, and particular 40-70 percent by weight of the total composition, and having a particle size of about 0.1-30 µm, preferably 0.8-20 µm, and particularly 1.2-10 µm.

The composition according to the present invention may also comprise one or more additional compounds selected from the group consisting of chlorhexidine, silica, and L-Fucose.

If chlorhexidine is included in the inventive composition the amount thereof is about 0.01-2, preferably 0.05-1.5, and particularly 0.1-1 percent by weight of the total composition, and having a particle size of about 3-300 µm, preferably 25-250 µm, and particularly 100-200 µm.

If silica is included in the inventive composition the amount thereof is about 0.1-10, preferably 0.35-7, and particularly 0.5-3 percent by weight of the total composition, and having a particle size of about 50-400 µm, preferably 100-350 µm, and particularly 150-250 µm.

If L-Fucose is included in the inventive composition the amount thereof is about 0.5-10, preferably 1-5, and particularly 1.5-3 percent by weight of the total composition, and having a particle size of about 200-800 µm, preferably 300-700 µm, and particularly 400-600 µm.

Since the inventive powder composition is to be administrated into the auditory canal, which is preferably done by a dispenser, the composition should form a light, fluffy powder.

Both lactose and kaolin are two effective absorbent of lipids and moisture keeping available lipids at a minimum, and both are highly hygroscopic that dry out the humid auditory canal removing the moisture necessary for Malassezia to multiply.

To demonstrate the usefulness of the powder composition according to the invention studies were undertaken against the discomfort dogs experience when there is a change in the normal balance of the microflora in the auditory canal.

In a first study, Example 1, the inventive composition with a small amount of added silica and without any antifungal or antibacterial ingredients was compared to an ordinary on the market existing powder composition comprising boric acid. 17 dogs that met certain criteria were included in and completed this study, and two veterinaries confirmed the presence of otitis externa by ocular exam, i.e. that the dogs exhibited clinical sign, such as erythema, pruritus, and head shaking.

The length of the study was three weeks and the dose administrated for the inventive composition was 0.15 grams per ear.

The study was conducted as follows:

i) The veterinary examined the dog and showed the owner of the dog how to administrate the powder composition.

ii) The owner of the dog administrated one dose per ear every day for six days.

iii) After day six the owner of the dog administrated one dose per week for two weeks.

iv) Three weeks after the veterinary had examined the dog, the dog was examined again by the veterinary. It should be noted that the results represent an overall evaluation of the clinical signs.

The result of this study is given in Example 1 below.

EXAMPLE 1

| Dog | Batch | Batch | Result |
| --- | --- | --- | --- |
| 1 | z2t | | Good |
| 2 | | y3q | Good |
| 3 | | y3q | Good |
| 4 | z2t | | Good |
| 7 | z2t | | Good |
| 8 | z2t | | Less good |
| 9 | z2t | | Less good |
| 10 | z2t | | Good |
| 11 | z2t | | Good |
| 12 | z2t | | Good |
| 13 | z2t | | Good |
| 14 | z2t | | Less good |
| 15 | z2t | | Good |
| 16 | | y3q | Less good |
| 17 | | y3q | Good |
| 18 | | y3q | Good |
| 19 | | y3q | Good | z2t is an existing powder composition comprising boric acid. y3q is the inventive composition containing 0.1 percent by weight lactic acid, 30.0 percent by weight lactose, 68.9 percent by weight kaolin, and 1.0 percent by weight silica.

In a further study, Example 2 below, 12 miniature schnauzers all exhibiting clinical sign such as pruritus and having black waxy substance in the auditory canal were treated with the inventive composition with added silica and chlorhexidine. The length of the study was 26 days. The first five days the dogs received one dose of 0.15 grams of the inventive powder composition per ear and day. From day 6 to day 26 the dogs received the same dose once a week. The auditory canal was not massaged and there was no wiping off of any excess powder in the auditory canal. Most of the time the dogs shook their heads and the excess was disposed of.

The inventive powder composition in Example 2 was composed of 0.1 percent by weight lactic acid, 30.0 percent by weight lactose, 68.75 percent by weight kaolin, 1.0 percent by weight silica, and 0.15 percent by weight chlorhexidine.

EXAMPLE 2

| | Day 0 | Day 5 | Day 12 | Day 19 | Day 26 |
| --- | --- | --- | --- | --- | --- |
| Dog 1 | Itching its ears, black waxy substance in the auditory canal | Does not itch its ears. The black substance is nearly gone | No itching, no black substance left, the auditory canal may be regarded as normal | Normal auditory canal | Normal auditory canal |

-continued

| | Day 0 | Day 5 | Day 12 | Day 19 | Day 26 |
|---|---|---|---|---|---|
| Dog 2 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 3 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 4 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 5 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 6 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 7 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 8 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 9 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 10 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 11 | Itching its ears, black waxy substance in the auditory canal | Does not itch its ears. The black substance is nearly gone | No itching, no black substance left, the auditory canal may be regarded as normal | Normal auditory canal | Normal auditory canal |
| Dog 12 | Itching its ears, black waxy substance in the auditory canal | Does not itch its ears. The black substance is nearly gone | No itching, no black substance left, the auditory canal may be regarded as normal | Normal auditory canal | Normal auditory canal |

In a further study only a few dogs having the same symptoms as the dogs in Example 1 were treated with the same dose regime as in said Example and with the inventive powder composition containing 0.01 percent by weight lactic acid, 30.0 percent by weight lactose, and 68.99 percent by weight kaolin, with added 1.0 percent by weight silica. The results of the treated dogs were similar to the results obtained in Example 1.

In the inventive powder composition the upper limit for the amount of lactic acid is about 2.0 percent by weight since tests have shown that this amount will give a pH of about 3, which is the lower limit that can be tolerated without causing irritation of the auditory canal.

Thus, the pH of the inventive powder composition should be within the range of about 3 to 4 which means that the same or essentially the same pH is obtained in the auditory canal of the patient at the dose regime set forth.

Although, all of the above-studied powder compositions contain silica, the inventors is of the opinion that silica may be excluded from the compositions, since the main feature of silica is to increase the flowability of the powder composition and the amount in the examples above is not more than 1.0 percent by weight of the total composition.

The amount of the other ingredients of the inventive composition, particularly regarding kaolin, lactose and silica, does not need to be particularly limited as long as they are within the limits stated above.

The onset dose given to small dogs is about 0.15 grams of the inventive composition per ear and day during the first 5 to 6 days, and for larger dogs this dose is about 0.30 grams and for the largest dogs this dose is about 0.45 grams. Due to the fact that most dogs will shake their heads, when given the inventive composition, some of the composition will be lost and will thus not reach the auditory canal.

It should also be noted that the inventor has realized that the inventive composition can be administrated for maintenance treatment so as to avoid ear problems of the above-mentioned types. The dose regime for maintenance treatment is about 0.05 to 0.45 grams per dose depending upon the size of the dog and ear given once a week.

It should be noted that the inventive powder composition was well tolerated and well accepted by the dogs and their owners and no adverse side effects were observed.

Furthermore, contrary to what may be expected when a power is poured into the ear no buildup of powder in the ear/auditory canal was reported.

A surprise finding in the studies was a significant lowering of excessive lipid/wax deposits in the auditory canals of the dogs which resulted in that the ears were significant cleaner at the end of the studies than on day one. Although, while not being bounded by any particular theory the inventor is of the opinion that once the inventive powder composition come in contact with a moist surface of the auditory canal it will dissolve and cling to the moist surface and thus absorb moisture and fatty substances, and subsequently after the moisture evaporate flakes or similar particles are formed that have a tendency to fall off which then may be shaken out from the ears of the dog.

It was concluded that the use of the inventive powder composition is a safe and an effective measure to reduce clinical signs of otitis externa, and that it may provide an alternative therapeutical and prophylactic approach to lower the risk of microbial overgrowth that can cause ear infections.

The invention claimed is:

1. A powder composition for treating and/or preventing a disorder in an auditory canal of a mammal, the disorder being selected from the group consisting of otitis externa and pyotraumatic folliculitus, wherein said powder composition consists of, in admixture: lactic acid, lactose and kaolin, wherein the amount of lactic acid is such that the pH of the powder composition is within the range of about 3 to 4, and wherein the powder composition is configured to be administered into the auditory canal of the mammal.

2. The powder composition according to claim 1, wherein the particle size of said lactic acid is 1-200 µm, the particle size of said lactose is 1-200 µm, and the particle size of said kaolin is 0.1-30 µm.

3. A powder composition according to claim 1 for use as a veterinary drug.

4. A powder composition according to claim 1, wherein the auditory canal is an auditory canal of a dog or a cat.

5. The powder composition according to claim 1, wherein the particle size of said lactic acid is 7.5-150 µm, the particle size of said lactose is 7.5-150 µm, and the particle size of said kaolin is 0.8-20 µm.

6. The powder composition according to claim 1, wherein the particle size of said lactic acid is 15-100 µm, the particle size of said lactose is 15-100 µm, and the particle size of said kaolin is 1.2-10 µm.

* * * * *